US005700653A

United States Patent [19]
Lu et al.

[11] Patent Number: 5,700,653
[45] Date of Patent: Dec. 23, 1997

[54] LIQUID STABLE THIOL ACTIVATOR

[75] Inventors: Carrie J. Lu, Fullerton; Fredrick S. Yein, Diamond Bar, both of Calif.

[73] Assignee: Beckman Instruments, Inc., Fullerton, Calif.

[21] Appl. No.: 541,473

[22] Filed: Oct. 9, 1995

Related U.S. Application Data

[63] Continuation of Ser. No. 239,260, May 6, 1994, abandoned.

[51] Int. Cl.$^6$ .................... C12Q 1/48; C12N 9/96
[52] U.S. Cl. .................... 435/15; 435/17; 435/188
[58] Field of Search .................. 435/15, 17, 183, 435/188, 194; 436/18

[56] References Cited

U.S. PATENT DOCUMENTS

| H622 | 4/1989 | Kageyama | 435/14 |
|---|---|---|---|
| 4,118,279 | 10/1978 | Determann | 195/63 |
| 4,339,533 | 7/1982 | Chu | 435/17 |
| 4,740,458 | 4/1988 | Kondo | 435/15 |
| 4,883,762 | 11/1989 | Hoskins | 436/18 |
| 4,888,289 | 12/1989 | Takami | 435/15 |
| 5,023,235 | 6/1991 | N'Guyen | 514/18 |
| 5,096,926 | 3/1992 | Fiorini et al. | 514/569 |
| 5,192,657 | 3/1993 | Jarway | 435/4 |
| 5,298,406 | 3/1994 | Loyd | 435/17 |

OTHER PUBLICATIONS

Sandifort; "Effects of Ethylene Diamine–tetraacetate on CK–NAC Reagent Starilay and Measured Creatine Kinase Activities", *Clin. Chem.* (23) 11, p. 2169 ets., (1977).

Nealon; "Activation of Human Creatine Kinase Isuenzymes By pH and Various Sulfhydryl and Chelating Agents", *Clin Chem*,(27) No. 3, p. 402 ets., (1981).

Horder, "IFCC Methods for the Measurement of Catalytic Concentrations of Enzymes"*JIFCC*, Feb. (1990) p. 26 et.s.

Greenwald, "Therapeutic Usages of Oxygen Radical Scavengers in Human Iron, and Metal Chelating Agents", *Free Rad. Res. Comm.*, vol 16, No. 1, pp. 1–10 (1992).

Zimmerman, "Therapeutic Application of Oxygen Radial Scavengers", *Chest*, (100), #3, p. 1895 ets, Sep. 1991.

Gee; "Clastogenic and Mutagenic Actions of Active Species Generated in the 6–Hydroxydopamine/Oxygen Reaction"; Effects of Scavengers of Active Oxygen.

Primary Examiner—Ralph Gitomer
Attorney, Agent, or Firm—William H. May; Margaret A. Kivinski

[57] ABSTRACT

An aqueous, liquid-stable thiol activator solution is disclosed. The solution can include a thiol activator, such as N-acetyl-L-cysteine and a stabilizing agent, such as mannitol. The thiol is stabilized in the aqueous solution for at least about one year under storage conditions and for at least about 28 days under open-bottle conditions. The solution can be used as a reactivator of creatine kinase catalytic activity.

18 Claims, No Drawings

LIQUID STABLE THIOL ACTIVATOR

This application is a continuation of application(s) Ser. No. 08/239,260 filed on May 6, 1994 now abandoned.

BACKGROUND

The present invention relates to a liquid stable thiol activator. In particular, the present invention relates to a liquid stable thiol activator solution useful as a reagent in an enzyme assay.

Diagnostic and therapeutic decision making can be assisted by reagents and methods which permit rapid, accurate, and reproducible detection and quantification of diverse biological molecules in various physiological fluids. A biological molecule of interest can be a naturally or artificially produced substance such as an amino acid, protein, nucleic acid, or steroid or a derivative or metabolite thereof. Physiological fluids include blood, plasma, serum, urine, amniotic, pleural and cerebrospinal fluid.

Not uncommonly, a biological molecule in a sample of a physiological fluid can be detected by detecting the activity, influence or effect of the biological molecule upon a substance in its environment, such as a substrate in solution with the biological molecule. When a test sample of a physiological fluid is removed from an in vivo environment into a non-biophysiological, in vitro environment, such as by drawing a sample of a patient's physiological fluid into a test tube, the activity of many biological molecules in the test sample will rapidly decline. Hence, to accurate assay an in vivo equivalent of the normal activity of a biological molecule, it is necessary to reactivate the biological molecule prior to or at the time of the in vitro assay for biological molecule activity. Many different thiol compounds have been used to reactivate diverse biological molecules of interest.

An enzyme is a protein capable of catalyzing a reaction with a suitable substrate. Detection and quantification of an enzyme, or the catalytic activity of an enzyme, present in a sample of a physiological fluid can provide important information about a bodily condition such as a disease state.

Creatine kinase[1] is an enzyme present in muscle tissue throughout the body and in the brain. Creatine kinase can catalyze a transfer of phosphate from phosphocreatine to adenosine diphosphate[2] thereby forming adenosine triphosphate[3]. Thus, creatine kinase catalyses the following reversible reaction in both directions:

Creatine phosphate+ADP⇌Creatine+ATP

[1]Also known as ATP:creatine N-phosphotransferase.
[2]ADP
[3]ATP

An assay for the catalytic activity of creatine kinase and its isoenzymes in patient physiological fluid samples is one of the most important clinical tests for the diagnosis of muscle lesions, heart disease, myocardial infarction, muscular diseases such as progressive muscular dystrophy, as well as for various nervous system diseases and mental disorders.

One of the most widely used tests for creatine kinase catalytic activity is the hexokinase/glucose-6-phosphate dehydrogenase assay, which can be referred to simply as the "creatine kinase assay". The creatine kinase assay is generally carried out using a spectrophotometer to measure the change in light absorption at a wavelength of about 340 nm[4] due to formation of reduced form β-nicotinamideadenine dinucleotide (phosphate) during the following reactions:

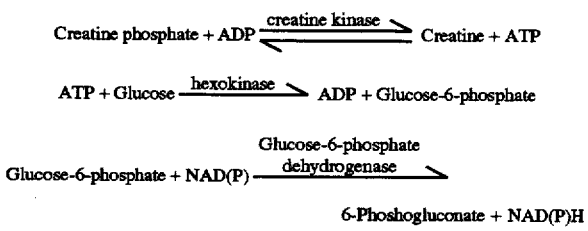

[4]"nm" is an abbreviation for nanometers, a measurement of wavelength.
SD/34P.app (39D-1120) 5.6.94

[4]"nm" is an abbreviation for nanometers, a measurement of wavelength.

The creatine kinase present in a sample of a physiological fluid becomes quickly, although reversibly, inactivated, upon removal from an in vivo environment. To accurately measure an in vivo equivalent of the creatine kinase activity in a test sample, the creatine kinase is reactivated to restore its catalytic activity. Reactivation can be accomplished by adding a suitable thiol compound to the test sample prior to carrying out the creatine kinase assay. Additionally, a chelator is often also added to the test sample prior to the assay for creatine kinase activity, to remove undesirable metal ions, such as $Fe^{++}$, which, if present, can inhibit the catalytic activity of the creatine kinase.

Various thiol[5] compounds, such as mercaptoethanol, monothioglycerol, glutathione and N-acetyl-L-cysteine[6] have been used to reactivate the creatine kinase present in a test sample of a physiological fluid.

[5]A thiol compound contains an —SH group.
[6]N-acetyl-L-cysteine can be referred to as "NAC".

A suitable thiol activator for creatine kinase must fulfill several requirements, including rapid and essentially complete reactivation of creatine kinase catalytic activity, no precipitation of proteins in the test sample, sufficient solubility in solution and lack of an obnoxious odor. Additionally, the thiol activator must also be capable of being freeze-dried and be usable upon liquification so that it can be incorporated into a lyophilized reagent kit. Furthermore, the liquified or reconstituted thiol activator must have at least some minimal stability while in solution, so that the thiol activator can have utility as a liquid reagent.

The thiol N-acetyl-L-cysteine meets these requirements and is known to be capable of restoring at least about 99% of creatine kinase catalytic activity in serum samples stored for one week at 4° C. Thus, N-acetyl-L-cysteine has been used as a reactivator of creatine kinase and is known to be stable as a dry crystalline powder suitable for reconstitution. It is believed that NAC acts by reducing oxidized sulfhydryl functional groups of creatine kinase thereby restoring creatine kinase catalytic activity.

Unfortunately, many thiol activators, including NAC, become unstable and rapidly deteriorate when in solution. Thus, many thiols are stored in powdered form. Deterioration of a thiol in solution is believed due to auto-oxidation of thiol sulfhydryl groups. Auto-oxidation of a thiol can be accelerated by the presence of certain polyvalent metal cations (such as $Fe^{++}$) in solution with the thiol.

An aqueous solution of the thiol activator NAC is stable for only about twenty-four hours at 4° C. Hence, use of an NAC solution prepared more than about 24 hours prior to its use as a reactivator of the creatine kinase present in a test sample of a physiological fluid, will not permit an accurate assay of the catalytic activity of the creatine kinase.

The deterioration of a thiol activator, such as NAC, in aqueous solution can be retarded somewhat by the addition of a chelator to the aqueous thiol solution. The chelator acts to remove certain metal ions from the thiol solution. Chelators such as EDTA[7], EGTA[8] and BHN[9] can be used to remove multivalent metal cations, such as $Fe^{++}$, from the thiol activator solution. Aqueous thiol stability is thereby improved. For example, adding suitable amounts of EDTA to an aqueous NAC solution stored at 4° C. is known to increase the stable life, and hence the utility, of the NAC present in the solution from about twenty-four hours to about 5 days.

[7]Ethylene diamine tetra acetic acid or ethylene diamine tetra acetate
[8]Ethylene glycol bis(β-aminoethyl ether)-N,N,N',N'-tetraacetate
[9]2,2-Bis(hydroxyethel)-2,2',2"-nitrilotriethanol Due to notorious instability in solution, thiol activators, such as NAC, are typically stored as lyophilized powders. The freeze-dried thiol powder is reconstituted with water at the time of use to activate a biological molecule.

Thiol reconstitution is error prone, time-consuming, can introduce various contaminants into the solution and is manifestly unsuited for high volume assays, such as enzyme chemistry clinical laboratories and hospital settings. Additionally, reconstitution of thiol powders prevents full utilization of the speed and efficiency of automated assay procedures and instrumentation which require large amounts of liquid stable reagents. Furthermore, reconstituted thiol solutions are unstable and rapidly deteriorate, even with inclusion of one or more chelators into the reconstituted thiol solution.

What is needed therefore is a liquid stable thiol solution and a method for making such a liquid stable thiol solution.

SUMMARY

The present invention encompasses a composition comprising a thiol activator for activating a biological molecule, a stabilizing agent capable of stabilizing the thiol activator in a liquid and a liquid capable of solubilizing the thiol activator, the stabilizing agent and the metal. Significantly, the thiol activator is stabilized in the liquid for an extended period.

The composition can also comprise a metal ion for facilitating the activity of the biological molecule and a chelator for removing other, undesired metal ions from the liquid.

Another embodiment of the present invention is a liquid stable thiol activator solution which can include a thiol activator, a stabilizing agent, such as a free radical scavenger, a metal ion, a chelator, and an aqueous buffer for solubilizing the thiol activator, the stabilizing agent, the metal ion and the chelator. Preferably, the buffer is capable of maintaining the liquid stable thiol activator solution at a physiological pH.

A method within the scope of the present invention for making a liquid stable thiol activator can have the steps of selecting a liquid capable of solubilizing a thiol activator, a stabilizing agent, a metal ion, and a chelator, adding a thiol activator to the buffer, adding a stabilizing agent to the buffer, adding a metal ion to the buffer, and adding a chelator to the buffer.

An assay for creatine kinase can be practiced according to the present invention by preparing a liquid stable thiol activator solution, adding a test sample to the liquid stable thiol activator solution, and detecting creatine kinase activity in the test sample.

The present invention also includes a method for preparing a stable aqueous solution of NAC, by adding EDTA and mannitol to the solution in predetermined concentrations. Finally, the present invention includes a aqueous reagent for assaying creatine kinase. This reagent can include a buffer for maintaining the liquid at a physiological pH, N-acetyl-L-cysteine, ethylene diamine tetra acetic acid, mannitol, magnesium and glucose. In this reagent the concentrations of ethylene diamine tetra acetic acid and mannitol are selected to improve the stability of the N-acetyl-L-cysteine in the buffer.

DESCRIPTION

The present invention is based upon the discovery that a liquid stable thiol activator solution can be made by adding a stabilizing agent to a liquid containing the thiol activator. Prior to our invention, a liquid stable thiol solution of a thiol activator, such as N-acetyl-L-cysteine, was unknown.

A suitable composition to use as a liquid stable thiol activator solution can contain a thiol activator for activating a biological molecule, a stabilizing agent capable of stabilizing the thiol activator in a liquid and a liquid capable of solubilizing the thiol activator, and the stabilizing agent. We have found that such a composition permits preparation of a solubilized thiol activator which is stabilized in the liquid for an extended period of time.

The thiol activator present in the solution can be any suitable thiol such as glutathione, 2-aminoethylisothiouronium bromide, thioglycolic acid, cysteine, mercaptoethanol, dithiothreitol, monothioglycerol, glutathione and N-acetyl-L-cysteine. Where the liquid stable thiol activator solution is used as a creatine kinase reagent, preferably the thiol activator is N-acetyl-L-cysteine because of its known effectiveness to reactivate creatine kinase.

The thiol activator can function to activate a variety of different biological molecules, including various enzymes, such as creatine kinase and fatty acid synthetase, and certain lipoproteins where the three dimensional conformational configuration (and hence biological activity) of the biological molecule depends, at least in part, upon the presence of an —SH group in the molecule.

The stabilizing agent present in the composition can be any substance capable of stabilizing the chosen thiol activator in solution. A variety of free radical scavengers, such as for example, inositol, tocopherol, mannitol, superoxide dimutase, catalase, glutathione peroxidase, N-2-mercaptopropionyl glycine, dimethyl thiourea, glutathione, the 21-aminosteroids, deferoxamine, allopurinol, dimethyl sulfoxide and coenzyme Q can be used as the stabilizing agent. Where the liquid stable thiol solution is used as a creatine kinase reagent, the stabilizing agent is preferably inositol or mannitol. We have found that mannitol is particularly well-suited to stabilize NAC in aqueous solution.

The free radical scavenger stabilizing agent can be used at a concentration of from about 5 mmol/L[10] to about 550 mmol/L in the aqueous thiol activator solution. Less than about 5 mmol/L of the free radical scavenger in the aqueous thiol solution does not provide enough free radical scavenger to stabilize a significant amount of the thiol. More than about 550 mmol/L of the free radical in the aqueous thiol solution can be difficult to solubilize in the solution. Preferably, the stabilizing agent is used in a concentration of from about 35 mmol/L to about 100 mmol/L in the aqueous thiol activator solution, as we have determined this to be an effective stabilizing agent concentration range.

[10]"mmol/L" means millimoles per liter, a measurement of the concentration of a solute in a solvent.

The free radical scavenger used as a stabilizing agent can be used in particular to stabilize the thiol present in a creatine kinase reagent. The creatine kinase reagent is used to reactivate the creatine kinase present in a sample of a physiological fluid. Typically, the creatine kinase assay detects reactivated creatine kinase catalytic activity through a spectrophotometric light absorption method. When a spectrophotometric assay method is used for this purpose, it is important that the stabilizing agent present in the thiol activator solution (which is used as a creatine kinase reagent) be substantially transparent to light at the measurement wavelength, and therefore not interfere unduly with the light absorption measurements used to assess creatine kinase catalytic activity. Frequently, a wavelength of less than about 600 to 700 nm, such as about 340 nm, is used to spectrophotometrically measure the light absorption increase due to creatine kinase catalytic activity during the creatine kinase assay.

When the liquid stable thiol activator solution is used as a reagent in the creatine kinase assay, the liquid component of the composition preferably comprises an imidazole buffer which has a low absorbance at the typical measurement wavelengths of from about 300 nm to about 700 nm typically used in the creatine kinase activity assay.

The liquid stable thiol solution can also contain a chelator. The chelator is believed to function by chelating undesired metallic ions, such as iron ions present in the thiol activator solution. If the solution does not contain any iron ions, then the need for a chelator in the solution is significantly reduced. A constraint on the amount of the chelator used is that one does not want to have so much present that chelation of excessive amounts of useful metal ions, such as Mg, present in the thiol activator solution can occur.

When a chelator, such as EDTA, EGTA or BHN is present in the aqueous thiol solution, the chelator is preferably used in a concentration of from about 0.025 mmol/L to about 4 mmol/L. Less than about 0.025 mmol/L of chelator in the aqueous thiol solution does not provide enough chelator to remove a significant amount of undesired metal ions which may be present in the solution. More than about 4 mmol/L of chelator can result in chelation of excessive amounts of useful metal ions, such as $Mg^{++}$. Magnesium cations play an important role in the creatine assay and are therefore desirable metal ions. More preferably, the chelator is present in the aqueous thiol solution in a concentration of from about 0.5 mmol/L to about 2 mmol/L, because we have determined this to be an effective chelator concentration range.

When an NAC solution is prepared for use as creatine kinase assay reagent and EDTA is also used in the aqueous NAC solution, preferably from about 35 mmol/L to about 100 mmol/L of mannitol or inositol and from about 0.5 mmol/L to about 2 mmol/L of EDTA is used in the aqueous NAC solution as we have found that such concentrations of mannitol and EDTA permit useful stabilized aqueous solutions of NAC to be prepared.

The liquid which is used in the composition can be any suitable liquid, such as water, which is capable of acting as a solvent for all the components of the composition at their desired concentrations. When the composition is used as a creatine kinase reagent, preferably the liquid is a buffered solution capable of maintaining the liquid at a physiological pH between about 6–8. Most preferably the pH of the creatine kinase reagent is about 6.7 at about 25° C. for most accurate enzyme measurement.

The liquid stable thiol solution can also contain a metal ion capable of facilitating the activity of the biological molecule. Where the biological molecule to be activated is creatine kinase, the metal ion is preferably a magnesium cation. The magnesium cation is believed to function by coordinating with ADP during the creatine kinase catalyzed phosphorylation of ADP to ATP.

The liquid stable thiol activator solution can be prepared by first selecting a buffer capable of solubilizing a thiol activator, a stabilizing agent, a metal ion, and a chelator. The next step in the method for making the solution is to add a thiol activator, a stabilizing agent, a metal ion, and a chelator to the buffer.

A significant aspect of the present invention is the discovery that the thiol activator present in the liquid of the composition can retain its activation ability substantially undiminished for at least about one year, when the composition is stored at about 4° C. in an air tight bottle or other container, protected from the light. The thiol activator in the composition of our invention is liquid stable under such storage conditions for as long as about two or three years.

Additionally, we have discovered that the thiol activator of a composition within the scope of our invention has an open-bottle (i.e. an in-use life during which aliquots of the solution of used and the remaining stock is stored in an open container at about 4° C. until the solution is again to be used) life during which the composition retains its thiol activation ability substantially unchanged for at least about 28 days. The stabilized thiol solution of our invention can maintain open bottle stability of the thiol present in the solution for 60 days or more after preparation and storage at 4° C. in an open bottle, without significant change to the stability of the thiol in the solution stored under such conditions.

By retention of thiol stability substantially unchanged, it is meant that the thiol solution of our invention can be used throughout the time periods indicated, under the storage conditions indicated, to reactivate a biological molecule placed in an in vitro environment to substantially an in vivo equivalent biological activity of the molecule.

The composition can also contain a sugar molecule, such as glucose, to assist formation of the detectable end product of the creatine kinase assay.

A preferred liquid stable thiol activator solution according to the present invention can include a thiol activator, a stabilizing agent, a metal ion, a chelator and a buffer capable of solubilizing these four components. The buffer is chosen to also be capable of maintaining the liquid stable thiol activator solution at a physiological pH. Such a solution we have found provides a solubilized thiol activator that is stable in the solution and a thiol activator which retains its thiol activation ability substantially undiminished.

The present invention permits preparation of a liquid stable reagent for assaying creatine kinase. This creatine kinase reagent does not contain any creatine kinase or any of the creatine kinase isoenzymes. The creatine kinase reagent can be an aqueous solution of a buffer for maintaining a physiological pH, N-acetyl-L-cysteine, ethylene diamine tetra acetic acid, mannitol, magnesium, and glucose, wherein the concentrations of ethylene diamine tetra acetic acid and mannitol are selected to improve the stability of the N-acetyl-L-cysteine in the buffer. A preferred creatine kinase reagent is an aqueous solution of liquid stable NAC in solution with EDTA and mannitol.

A further method according to our invention is for preparing a stable aqueous solution of NAC by adding EDTA, mannitol, magnesium cation and NAC in suitable concentrations to a buffer solution.

Our invention also includes within its scope an assay for creatine kinase. This assay can be carried out preparing a liquid stable thiol activator, adding a test sample to the liquid stable thiol activator, and detecting creatine kinase in the test sample. The present invention provides a stable aqueous NAC solution which can be used as a creatine kinase reagent to reactivate creatine kinase in a test sample. The present invention does not encompass a creatine kinase control reagent for maintaining the activity of the creatine kinase present in the creatine kinase control reagent.

The creatine kinase reagent preferably contains mannitol or inositol and NAC in aqueous solution. We found that mannitol has a significant stabilization effect on the NAC in aqueous solution. Most preferably, mannitol and EDTA are both used in the aqueous NAC solution.

With the combination of EDTA and mannitol, we found that NAC activity in a creatine kinase reagent recovered 96% after stress at 41° C. for 28 days; for open bottle on-instrument stability (2° to 8° C.), NAC activity in creatine kinase buffer recovered 100% after 28 days on a SYNCHRON® CX4CE® clinical chemistry auto analyzer (Beckman Instruments, Inc.). However, without EDTA and mannitol in creatine kinase buffer, NAC activity lost completely after stress at 41° C. for 13 days.

Adding 35.0 mmol/L mannitol in creatine kinase buffer, allowed the EDTA concentration to be reduced from 2.0 to 0.50 mmol/L, while maintaining the same stability of the NAC in the aqueous solution. A lower EDTA concentration in the creatine kinase reagent is preferred so as to reduce the chelating of $Mg^{+2}$ by the EDTA.

EXAMPLES

Example 1

(Preparation of Creatine Kinase Buffer Reagent)

A creatine kinase buffer solution was prepared to contain 118.9 mmol/L of imidazole (molecular weight 68.1) (Calbiochem, San Diego, Calif.), 11.89 mmol/L of Mg Acetate($H_2O$)$_4$ (mol. wt. 214.5) (J. T. Baker, Inc.), 23.8 mmol/L of D-Glucose (mol wt 180.2) (Pfanstiehl Labs, Inc.), and 23.77 mmol/L of N-acetyl-L-cysteine (mol wt 163.2) (Boehringer Mannheim Biochemicals, Indianapolis, Ind.).

The solvent used for all the buffer solutions was deionized water. The buffer solution pH was adjusted to 6.7 at 25° C. using either glacial acetic acid or a 1 mol/L solution of aqueous imidazole.

Additional creatine buffer solutions were also prepared to contain EDTA disodium (mol wt 372.20) and mannitol (mol wt 182.17) in the concentration ranges previously set forth, as reflected by the following tables.

The creatine kinase assays were carried out using a Beckman Instruments, Inc. (Fullerton, Calif.) SYNCHRON® Clinical Chemistry Autoanalyzer. The SYNCHRON® instrument uses a three reagent (A, B and C) compartment cartridge system. Compartment A contains a creatine kinase buffer solution made as set forth above. Compartment B carries the pH 6.5 coenzyme solution for the hexokinase/glucose-6-phosphate dehydrogenase assay for creatine kinase. The SYNCHRON® cartridge Compartment B coenzyme solution was made by dissolving into deionized water, at least, suitable amounts of hexokinase, G6PDH, AMP, NADP, ADP, and P',P$^5$-Dipenta-P. Compartment C contained the enzyme substrate prepared by mixing into deionized water, at least, creatine phosphate and adjusting the pH to 8.5.

A test sample aliquot of about 12 µL is analyzed by the SYNCHRON® instrument, which adds 222 µL of the compartment A buffer, 22 µL of the compartment B solution and 20 µL of the compartment C solution at the time of conducting the creatine kinase assay.

Example 2

(NAC Assay Procedure)

NAC stability studies were carried out to determine the stability of NAC in the compartment A creatine kinase buffer reagent.

NAC concentrations were assayed for all of the creatine kinase buffer solutions prepared using Ellman's reagent, which determines free SH groups[11]. The relevant NAC assay reaction is:

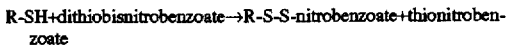
R-SH+dithiobisnitrobenzoate→R-S-S-nitrobenzoate+thionitrobenzoate

[11]As set forth by Ellman, G. L., et al., Biochem. Pharmacol. 7, 88 (1961)

The optical absorbance of the reaction solution was measured at 405 nm using a DU®7500 spectrophotometer (Beckman Instruments, Inc.).

Example 3

(EDTA as a Stabilizer of NAC in Creatine Kinase Buffer)

An experiment was carried out to confirm that, as known in the art, NAC in a solution of creatine kinase buffer will become unstable in the buffer solution, but that the presence of EDTA can provide some limited stability to an aqueous NAC solution.

Eight creatine kinase buffer solutions (A to H) with pH 6.7 were prepared, as shown by Table 1, to set up a fractional-factorial screening experiment. These eight solutions were prepared with or without imidazole, magnesium acetate, D-glucose and EDTA as shown by Table 1 where "1" means the component is present and "0" means the component was absent from the creatine kinase buffer solution.

Each of the eight solutions was prepared with 0.388 g NAC/100 ml. When imidazole was present, it was present at the concentration of 0.810 g/100 ml. When Mg acetate was present it was present at the concentration of 0.255 g/100 ml. When glucose was present, it was present at the concentration of 0.429 g/100 ml. And when EDTA was present in one of the eight creatine kinase buffer solutions prepared (as shown by Table 1), it was present in the concentration of 0.089 g EDTA/100 ml of the creatine kinase buffer solution.

The day of solution preparation was recorded as "day 0". Half of each solution (50 ml) prepared was stored at 5° C., while the remaining half (the other 50 ml) of each of the eight creatine kinase buffer solutions prepared was stored at 41° C. Thus, 5° C. and 41° C. stress tests (of NAC aqueous stability) of one half of each of the eight creatine kinase buffer solutions prepared were carried out.

On days 3, 5, 7, and 13 subsequent to buffer preparation, the Ellman's reagent assay for NAC was carried out and the results read using the DU®7500 spectrophotometer set at 405 nm to measure the absorption units A, as shown in the accompanying tables.

Table 2 shows the results of the 41° C. stress test. When EDTA was absent (i.e. creatine kinase buffer solutions C, D, G and H), the NAC present in the creatine kinase buffer solution rapidly became unstable. The presence of EDTA in the creatine kinase buffer solution, as expected, delayed significant NAC deterioration until about five days after buffer preparation. Thus, aqueous NAC stability improved significantly when 2.0 mmol/L of EDTA was present in the creatine kinase buffer solution.

Example Four (Effect of Mannitol on NAC Stability in Creatine Kinase Buffer)

Mannitol was added to creatine kinase buffer solutions which did not contain any of EDTA. It was found that when 59 mmol/L (0.9 g/100 ml) of mannitol was present in the creatine kinase buffer the NAC stress stability (at 41° C.), improved significantly. Thus, it was found that the NAC activity decreased by only about 30% after stress of the NAC containing buffer solution at 41° C. for 13 days. When both mannitol and EDTA were absent from the buffer, NAC stability became negligible after about the thirteenth day of the 41° C. stress test, as shown by Table 3. Thus, it was discovered that mannitol can itself provide significant stability maintenance for the NAC present in the aqueous creatine kinase buffer solution.

Example Five (Effect of Presence of EDTA and Mannitol Combination on Stability of NAC in Creatine Kinase Buffer)

It was found that the combination of EDTA and mannitol significantly improved the stability of NAC in the creatine kinase buffer, as compared to the effect on NAC stability of either EDTA or mannitol alone.

To determine the effect of the combination of EDTA and mannitol on NAC stability in creatine kinase buffer, factorial experiments were designed to optimize the concentration of EDTA and mannitol in the buffer. Thus, four creatine kinase buffer solutions, numbered 1 through 4, were prepared, as set forth by Table 4. Other combinations (not shown) of mannitol and EDTA at differing concentrations were also carried out (i.e. mannitol concentrations of 50, 75 and 100 mmol/L and EDTA concentrations of 0.5, 1 and 1.5 mmol/L). The results showed that by adding 35 mmol/L of mannitol, the EDTA concentration in the creatine kinase can be reduced from 2.0 mmol/L to 0.50 mmol/L, while still maintaining the same stability of NAC in creatine kinase buffer (see Table 5, where the 1–4 solutions are the same 1–4 solutions set forth in Table 4). It is preferred to have such a lower EDTA concentration in the creatine kinase buffer so as to reduce the chelating of $Mg^{+2}$ cations by the EDTA.

As shown by Table 6, the combination of 1.18 mmol/L of EDTA and 59.0 mmol/L of mannitol (i.e. solution 4 in Tables 4 and 5) was the optimum condition to stabilize NAC in the pH 6.7 creatine kinase buffer. The results showed that NAC activity in the creatine kinase buffer recovered 96% after stress at 41 ° C for 28 days. For on-instrument (i.e. open bottle use) stability (2° to 8° C. storage of the thiol activator solution), NAC activity in the creatine kinase buffer was essentially still 100% after 28 days of open bottle life and use in conjunction with a SYNCHRON® CX4CE® (see Table 6).

Although the present invention has been described in considerable detail with regard to certain preferred embodiments thereof, other embodiments within the scope of the teachings of the present invention are possible. For example, a wide variety of thiols, stabilizing agents and chelators are within the scope of the claimed compositions and methods.

TABLE 1

The Composition of Eight Different Creatine Kinase Buffer ("CK") Solutions

| CK Buffer Solution | NAC | Imidazole | Mg Acetate | Glucose | EDTA |
|---|---|---|---|---|---|
| A | 1 | 0 | 0 | 1 | 1 |
| B | 1 | 1 | 0 | 0 | 1 |
| C | 1 | 0 | 0 | 0 | 0 |

TABLE 1-continued

The Composition of Eight Different Creatine Kinase Buffer ("CK") Solutions

| CK Buffer Solution | NAC | Imidazole | Mg Acetate | Glucose | EDTA |
|---|---|---|---|---|---|
| D | 1 | 1 | 0 | 1 | 0 |
| E | 1 | 1 | 1 | 1 | 1 |
| F | 1 | 0 | 1 | 0 | 1 |
| G | 1 | 0 | 1 | 1 | 0 |
| H | 1 | 1 | 1 | 0 | 0 |

TABLE 2

Results of Screening Experiment-NAC Recovery in Creatine kinase Buffer

| 41° C. CK Buffer Solution | Absorbance (A) | | | | |
|---|---|---|---|---|---|
| | Day 0 | Day 3 | Day 5 | Day 7 | Day 13 |
| A | 2.095 | 2.087 | 2.042 | 2.041 | 2.062 |
| B | 2.150 | 2.065 | 2.050 | 2.091 | 2.053 |
| C | 2.038 | 2.078 | 1.880 | 1.561 | 0.739 |
| D | 2.045 | 1.983 | 1.840 | 1.698 | 1.211 |
| E | 2.037 | 2.113 | 2.039 | 2.050 | 2.026 |
| F | 2.058 | 2.117 | 2.026 | 2.016 | 1.854 |
| G | 2.042 | 1.988 | 1.850 | 1.657 | 1.150 |
| H | 1.934 | 1.739 | 1.347 | 0.960 | 0.175 |

TABLE 3

Effect of Mannitol on NAC Stability in Creatine kinase Buffer (without EDTA)

| 41° C. CK Buffer Solution | Absorbance (A) | | | | |
|---|---|---|---|---|---|
| | Day 0 | Day 3 | Day 5 | Day 7 | Day 13 |
| With Mannitol | 1.979 | 1.883 | 1.772 | 1.541 | 1.133 |
| Without Mannitol | 1.983 | 1.575 | 1.192 | 0.792 | 0.00 |

TABLE 4

Optimization Experiment - Effect of the Combination of EDTA and Mannitol on NAC Stability in Creatine kinase Buffer

| CK Buffer Solution | Mannitol mmol/L | EDTA mmol/L |
|---|---|---|
| 1 | 59 | 0.88 |
| 2 | 41.6 | 0.88 |
| 3 | 41.6 | 1.18 |
| 4 | 59 | 1.18 |

TABLE 5

Results of Optimization Experiment - NAC
Recovery in Creatine Kinase Buffer

| 41° C. CK Buffer | Absorbance (A) | | | |
|---|---|---|---|---|
| Solution | Day 0 | Day 6 | Day 10 | Day 15 |
| 1 | 2.265 | 2.127 | 2.161 | 2.072 |
| 2 | 1.156 | 1.084 | 1.067 | 1.006 |
| 3 | 2.217 | 2.127 | 2.117 | 2.039 |
| 4 | 2.182 | 2.143 | 2.077 | 1.916 |

TABLE 6

NAC On-Instrument Stability (2 to 8° C.)-NAC
Recovery in Creatine Kinase Buffer with EDTA and Mannitol

| Day 0 | Day 4 | Day 7 | Day 10 | Day 14 | Day 21 | Day 28 |
|---|---|---|---|---|---|---|
| 2.028 | 2.076 | 2.068 | 2.073 | 2.071 | 2.060 | 2.067 |

We claim:

1. A stabilized thiol activating composition, comprising:
   (a) a thiol which activates an enzyme;
   (b) a stabilizing agent which stabilizes the thiol, wherein the stabilizing agent is a free radical scavenger;
   (c) magnesium ion for facilitating activation of the enzyme; and
   (d) a liquid which solubilizes the thiol, the stabilizing agent, and the magnesium ion, wherein the thiol is stabilized in the liquid by the stabilizing agent, and wherein the composition is substantially free of any creatine kinase, said free radical scavenger is selected from the group consisting of inositol, tocopherol, mannitol, superoxide dismutase, catalase, glutathione peroxidase, N-2-mercaptopropionyl glycine, dimethyl thiourea, glutathione, 21-aminosteroids, deferoxamine, allopurinol, dimethyl sulfoxide and coenzyme Q.

2. The composition of claim 1, wherein the thiol is selected from the group consisting of glutathione, 2-aminoethylisothiouronium bromide, thioglycolic acid, cysteine, mercaptoethanol, dithiothreitol, monothioglycerol and N-acetyl-L-cysteine.

3. The composition of claim 2, wherein the thiol is N-acetyl-L-cysteine.

4. The composition of claim 1, further comprising an iron chelator for removing undesired iron ions from the liquid.

5. The composition of claim 4, wherein the iron chelator is present in the liquid in a concentration of from about 0.025 mmol/L to about 4 mmol/L.

6. The composition of claim 4, wherein the chelator is selected from the group consisting of ethylene diamine tetra acetic acid, ethylene glycol bis(beta-aminoethyl ether)-N,N,N',N'-tetraacetate and 2,2-bis(hydroxyethyl)-2,2',2"-nitrilotriethanol.

7. The composition of claim 1, wherein the thiol retains a substantially undiminished thiol activation ability for at least about one year under storage conditions.

8. The composition of claim 1, wherein the thiol retains a substantially undiminished thiol activation ability for at least about two years under storage conditions.

9. The composition of claim 1, wherein the thiol retains a substantially undiminished thiol activation ability for at least about 28 days under open bottle conditions.

10. The composition of claim 1, wherein the thiol retains a substantially undiminished thiol activation ability for at least about 60 days under open bottle conditions.

11. The composition of claim 1, wherein the stabilizing agent is present in the liquid at a concentration of from about composition 5 mmol/L to about 550 mmol/L.

12. The composition of claim 1, wherein the free radical scavenger is inositol.

13. The composition of claim 1, wherein the liquid comprises a buffered aqueous solution capable of maintaining the liquid at a pH between about pH 6 and pH 8.

14. A method for making a liquid stabilized thiol activating solution, comprising the steps of:
   (a) selecting a thiol which activates an enzyme;
   (b) adding the thiol to a liquid which solubilizes the thiol;
   (c) adding magnesium ion to the liquid; and
   (d) adding a stabilized agent to the liquid, the stabilizing agent stabilizing the thiol solubilized in the liquid, wherein the stabilizing agent is a free radical scavenger selected from the group consisting of inositol, tocopherol, mannitol, superoxide dismutase, catalase, glutathione peroxidase, N-2-mercaptopropionyl glycine, dimethyl thiourea, glutathione, 21-aminosteroids, deferoxamine, allopurinol, dimethyl sulfoxide and coenzyme Q, thereby making a liquid stable thiol solution wherein the thiol is stable in the solution and retains its thiol activation ability substantially undiminished for at least about one year under storage conditions and for at least about 28 days under open bottle conditions; said solution being substantially free of treating kinase.

15. A method for preparing a stabilized aqueous activating solution of N-acetyl-L-cysteine, comprising the steps of:
   (a) selecting an aqueous buffer;
   (b) adding ethylene diamine tetra acetate to an aqueous buffer;
   (c) adding N-acetyl-L-cysteine to the buffer;
   (d) adding magnesium ion to the buffer; and
   (e) adding mannitol to the buffer, wherein the buffer is capable of solubilizing the ethylene diamine tetra acetate and the mannitol, the method resulting in a stable aqueous solution of N-acetyl-L-cysteine, said solution being substantially free of creatine kinase.

16. An assay for creatine kinase activity, comprising the steps of:
   (a) preparing a liquid stable thiol solution by adding ethylene diamine tetra acetate, N-acetyl-L-cysteine, magnesium ion, and mannitol to an aqueous buffer;
   (b) adding a test sample of a physiological fluid to the liquid stable thiol, wherein the physiological fluid is selected from the group consisting of blood, plasma, serum, urine, amniotic, pleural and cerebrospinal fluid;
   (c) spectrophotometrically detecting a change in light absorption of the solution; and
   (d) correlating the creatine kinase activity in the test sample with the change in light absorption.

17. A liquid stabilized thiol activating composition comprising:
   (a) a thiol which activates an enzyme;
   (b) a free radical scavenger which stabilizes the thiol;
   (c) magnesium ion;
   (d) iron chelator; and
   (e) an aqueous buffer which solubilizes the thiol, the free radical scavenger, the magnesium ion and the iron chelator in the buffer, to thereby form a liquid stable thiol solution stable against significant deterioration of the thiol present in the solution for at least about one year under storage conditions and for at least about 28 days under open bottle conditions, said solution being substantially free of any creatine kinase, and wherein said free radical scavenger is selected from the group consisting of inositol, tocopherol, mannitol, superoxide dismutase, catalase, glutathione peroxidase, N-2-mercaptopropionyl glycine, dimethyl thiourea, glutathione, 21-aminosteroids, deferoxamine, allopurinol, dimethyl sulfoxide and coenzyme Q.

18. A reagent for a creatine kinase assay, comprising:

(a) an aqueous buffer;

(b) an enzyme activating amount of N-acetyl-L-cysteine;

(c) between about 0.025 mmol/L and about 4 mmol/L ethylene diamine tetra acetic add;

(d) between about 5 mmol/L and about 550 mmol/L mannitol; and (e) about 12 mmol/L magnesium ion, said reagent being substantially free of creatine kinase.

* * * * *